United States Patent [19]
Yabe et al.

[11] Patent Number: 5,458,133
[45] Date of Patent: Oct. 17, 1995

[54] COVER TYPE ENDOSCOPE APPARATUS

[75] Inventors: Hisao Yabe; Hideo Itoh, both of Hachioji; Yoshio Tashiro, Hino; Yoshihiro Iida, Tama; Akira Suzuki, Hachioji; Minoru Yamazaki, Hachioji; Osamu Tamada, Hachioji; Shigeru Nakajima, Hachioji; Keiichi Arai, Hachioji, all of Japan

[73] Assignee: Olympus Optical Co., Ltd., Tokyo, Japan

[21] Appl. No.: 53,453

[22] Filed: Apr. 28, 1993

[30] Foreign Application Priority Data

Mar. 15, 1993 [JP] Japan ................. 5-011194 U
Mar. 15, 1993 [JP] Japan ................. 5-011195 U
Mar. 15, 1993 [JP] Japan ................. 5-011196 U

[51] Int. Cl.$^6$ ........................................ A61B 1/00
[52] U.S. Cl. .................. 600/122; 600/109; 600/124; 600/133
[58] Field of Search ................... 128/4, 6, 917, 128/918, 919, 844

[56] References Cited

U.S. PATENT DOCUMENTS

| | | | |
|---|---|---|---|
| Re. 34,110 | 9/1992 | Opie. | |
| 3,162,190 | 12/1964 | Del Gizzo. | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahshi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,359,991 | 11/1994 | Takahashi et al. | 128/4 |

FOREIGN PATENT DOCUMENTS

| | | |
|---|---|---|
| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |

(List continued on next page.)

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

A cover type endoscope apparatus includes a cover, a covered endoscope which is inserted into this cover and used, and a cover holder for holding various peripheral units connected to the covered endoscope and the cover, wherein an indication device for indicating whether or not an apparatus should handle a clean area in a sterile state or other area is provided in each of the components.

18 Claims, 11 Drawing Sheets

FOREIGN PATENT DOCUMENTS 3-101901  10/1991  Japan.
3-101902  10/1991  Japan.
4-325138  11/1992  Japan.

COVER TYPE ENDOSCOPE APPARATUS

BACKGROUND OF THE INVENTION

1. Field of the Invention

The present invention relates to a cover type endoscope apparatus for examining body cavities, such endoscope apparatus having a covered endoscope mounted thereon.

2. Description of the Related Art

In recent years, endoscopes have come to be widely used not only in the industrial, but in the medical field as well. In the medical field, endoscopes are inserted into the living beings so as to observe or treat diseased parts. Since it is inserted into living beings, a patient's body liquids or mucin may adhere to the observation window disposed on the tip portion of the insertion portion of the endoscope, making it impossible to fully observe diseased parts. Accordingly, an endoscope apparatus is provided with an air and water supply mechanism, capable of supplying liquid to an observation window, for cleaning and blowing off water remaining on the observation window by using supplied air. These air and water supply functions are performed via air and water supply tubes by operating buttons disposed on the hand side of the endoscope.

Some endoscopes are provided with a suction tube for sucking in waste or mucin from living beings and discharging them outside the living beings, and with a treatment tool channel (a clamp channel) through which a treatment tool is passed for performing treatment. As described above, a plurality of sucion tubes, treatment tool channels or the like as well as air and water supply tubes are provided.

It is necessary to quickly clean and sterilize endoscopes which have been used for treatment so that it can be used for the next patient. However, the process for completely cleaning and sterilizing the endoscope is laborious and time-consuming, causing reduced efficiency.

Due to the above, recently, such a cover type endoscope apparatus is used that the cleaning and sterilizing of an endoscope is simplified by using, for each case, the endoscope covered with a cover and discarding the cover after the treatment is finished.

Only the tubes to be opened inside the living beings of a patient are provided on the cover side of this type of endoscope. The cover type endoscope provided with observation means or illumination means is covered with a cover so as to prevent it from being directly in contact with living beings.

The above cover type endoscopes have been disclosed in, for example, U.S. Pat. Nos. 4,646,722 and 3,162,190.

When the cover type endoscope apparatus is used for examination or the like, it has been required that this apparatus be classified as an apparatus which should be used in a clean area where a sterile state must be reliably secured immediately before examination and an apparatus which should be used in an area other than the clean area (hereinafter described as a general area) and that preparation, examination, treatment and disposal thereof be performed. Therefore, since persons in charge of their respective areas reliably manage apparatuses in areas in charge on their own responsibility and have always made efforts to perform careful and quick operations while they accurately judge which apparatus is to be used in a clean area so that the clean area is not contaminated.

However, with cover type endoscope apparatuses, indications such that which apparatus should be used in a clean or general area have not been made. Therefore, working with a cover type endoscope apparatus is a frustrating operation such that the mental strain continues because the operator cannot make a quick judgment whether the apparatus should be used in a clean or a general area.

Figure 1:
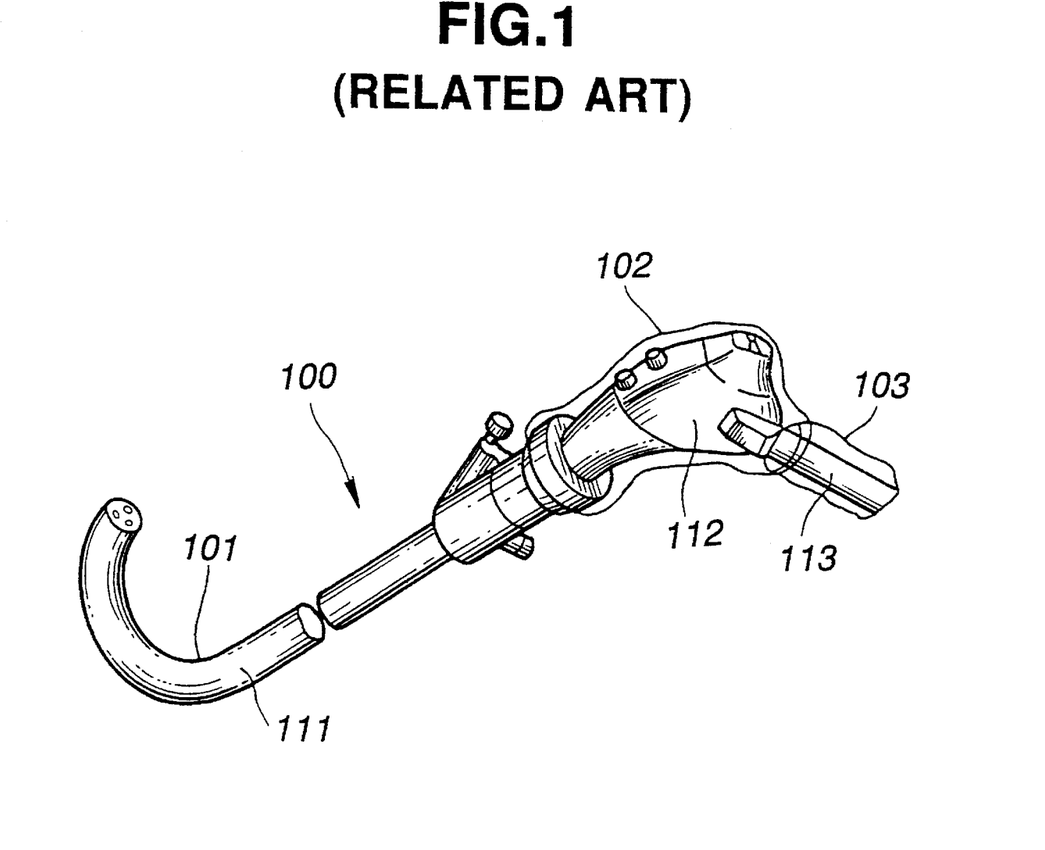
FIG. 1 is a perspective view schematically illustrating the construction of the cover of a conventional cover type endoscope.

As shown in FIG. 1, a cover 100 which covers a cover type endoscope apparatus is formed of: an insertion portion cover 101 into which a Cover type endoscope insertion portion 111 is inserted; an operation portion cover 102, formed of a soft, thin resin sheet, which covers a cover type endoscope operation portion cover 112; and a universal cord cover 103, formed of a soft, thin resin sheet, which covers a cover type endoscope universal cord 113.

However, an operation for covering an operation portion of the cover type endoscope which has a complex curved surface or irregular portions with a sheet cover in a liquid-tight manner and in such a manner as to be capable of easily grasping it, or for covering a universal cord extending from the cover type endoscope, an extending tube disposed on the cover or the like integrally and in liquid-sealing manner, is a difficult operation requiring dexterity.

SUMMARY OF THE INVENTION

It is an object of the present invention to provide a cover type endoscope apparatus for which it can be reliably and easily determined whether it should be used in a clean or a general area.

It is another object of the present invention to provide a cover type endoscope apparatus which is capable of being covered easily in a liquid-tight manner without deteriorating grasping characteristics or maneuverability of the cover type endoscope operation portion.

It is still another object of the present invention to provide a cover type endoscope apparatus which is capable of easily integrally covering a universal cord extending from the cover type endoscope, a tube extending from the cover or the like.

In short, the cover type endoscope apparatus in accordance with the present invention comprises: a cover which constitutes a cover type endoscope; a cover type endoscope which is inserted into a cover and used; various peripheral units connected to the cover type endoscope; and a cover holder for holding the cover. The cover type endoscope apparatus is provided with indication means for indicating whether an apparatus should be operated in a sterilized, clean or other area.

The above and further objects and novel features of the invention will more fully appear from the following detailed description when the same is read in connection with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

The first embodiment will be explained with reference to FIG. 2.

Figure 2:
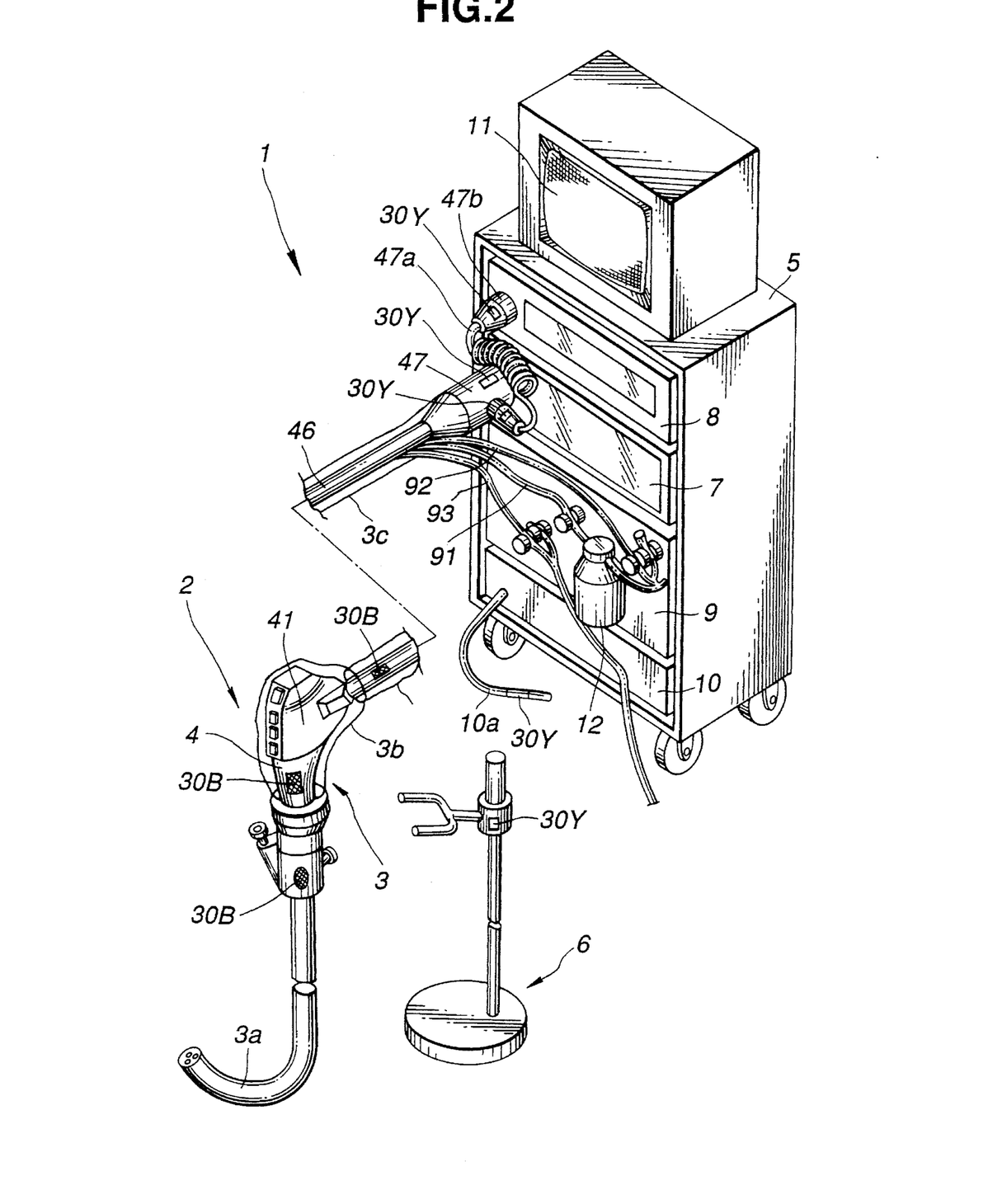
FIG. 2 is a perspective view illustrating the construction of a cover type endoscope apparatus in accordance with a first embodiment of the present invention.

As shown in FIG. 2, a cover type endoscope apparatus 1 of the first embodiment comprises a cover type endoscope 2 and a cover holder 2 for holding various peripheral units and the cover type endoscope 2. The cover type endoscope 2 comprises a cover 3 and a covered endoscope 4. The various peripheral units connected to the cover type endoscope 2 are housed in a cart 5.

The various peripheral units housed in the cart 5 include a light source apparatus 7 for supplying illumination light to an illumination optical system of the cover type endoscope 4 inserted into body cavities; a video processor 8 for displaying an endoscope image on a monitor (which will be described later) through a connection cable 47a connected to a connector 47 of the covered endoscope 4 by converting electrical signals from an imaging element disposed in an observation optical system of the covered endoscope 4 inserted into body cavities into video signals; a fluid control apparatus 9 for supplying water and air and sucking them, to which apparatus a water supply tube 91, an air supply tube 92 and a suction tube 93 are connected; an endoscope cover expander 10 (hereinafter referred to as an expander) which supplies air to the endoscope cover 3 so as to enable the covered endoscope 4 to be easily mounted or removed. A monitor 11 on which an endoscope image is displayed is placed on the top plate of the cart 5.

The cover type endoscope apparatus 1 is provided with indication means 30 for indicating a clean area of the parts which constitute the cover type endoscope apparatus 1, in which area a sterilized state must be reliably maintained, or other general area.

A tape, for example, a blue colored tape 30B for indicating a clean area is affixed on an insertion portion cover 3a of the cover 3 which is regarded as a clean area of the cover type endoscope apparatus 1, an operation portion cover 3b and a universal cord cover 3c. A tape, for example, a yellow colored tape 30Y, for indicating a general area is affixed on the covered endoscope 4, a connection cable 47a, a connection cable connector 47b, an extension tube 10a, a cover holder 6, the connector 47 for a universal cord or the like, all of the foregoing are regarded as general areas.

Since the blue tape 30B is affixed on the indication means 30 to indicate a clean area and a yellow tape 30Y is affixed thereon to indicate a general area as described above, a person in charge can easily recognize whether an area is a clean or a general area.

When an endoscope examination is carried out by using a cover type endoscope apparatus as described above, a person in charge of a work area is able to easily and quickly recognize whether an area is a clean or a general area. Therefore, since the operator can recognize whether he is working in a clean area or a general area, he can work without having to be too careful, and thus the clean area can be prevented from being inadvertently contaminated.

The indication means for indicating whether an area is a clean or a general area of the cover type endoscope apparatus is not limited to being a blue or yellow tape. Rather, in the indication means, colors to be displayed and display areas may be appropriately combined. Also, the indication means is not limited to being a color display, but symbols or characters may be used, or a combination of symbols and characters may be used.

Besides the above-described use, the indication means may be used as described below. When an endoscope examination is to be carried out, usually a check is made to determine whether a patient has an infectious disease, such as viral hepatitis, in an examination before the endoscope examination is carried out. Therefore, it is possible to separate apparatuses used for patients having an infectious disease from those used for general patients and separately discard the apparatuses (except in an emergency) because whether a patient has an infectious disease is known. However, even if apparatuses are separately discarded, it is impossible for those not in charge of the apparatuses to make a judgment whether they have been used for patients with an infectious disease.

Accordingly, when the cover type endoscope apparatus 1 is used for a patient with an infectious disease, a tape, for example, a red tape, is affixed on apparatuses to be used for a patient with an infectious disease beforehand to indicate that the apparatuses are to be used for a patient with an infectious disease.

The affixing of a red tape indicating that a cover type endoscope apparatus is to be used for a patient with an infectious disease in the above-described way makes it possible for a person in charge to recognize beforehand that a patient has an infectious disease. Further, apparatuses used for patients with an infectious disease can be discarded with accuracy separately from general apparatuses used for general patiens. In addition, the affixing of a red tape on discarded apparatuses makes it possible for doctors other than the dosctor in charge or nurses to easily recognize that discarded apparatuses have been used for a patient with an infectious disease.

It goes without saying that indication means for indicating that an apparatus is to be used for a patient with an infectious disease can be used in the same way as indication means for indicating a clean or general area is not limited to being a red tape, but any desired color may be selected. Furthermore, the indication means is not limited to being a color display, but symbols or characters may be used, or a combination of symbols and characters may be used.

In a case where one person should be in charge and this person has to work in both clean and general areas alternately, it is necessary to wear work gloves suitable for each of these work areas. However, since work gloves which has been used hitherto fits the hands of a wearer too tightly, it is very difficult to take off these work gloves. Therefore, there is a risk in that when a work glove is replaced hastily or removed carelessly, stains may adhere to a clean area. Accordingly, work gloves are formed as described below.

Figure 3:
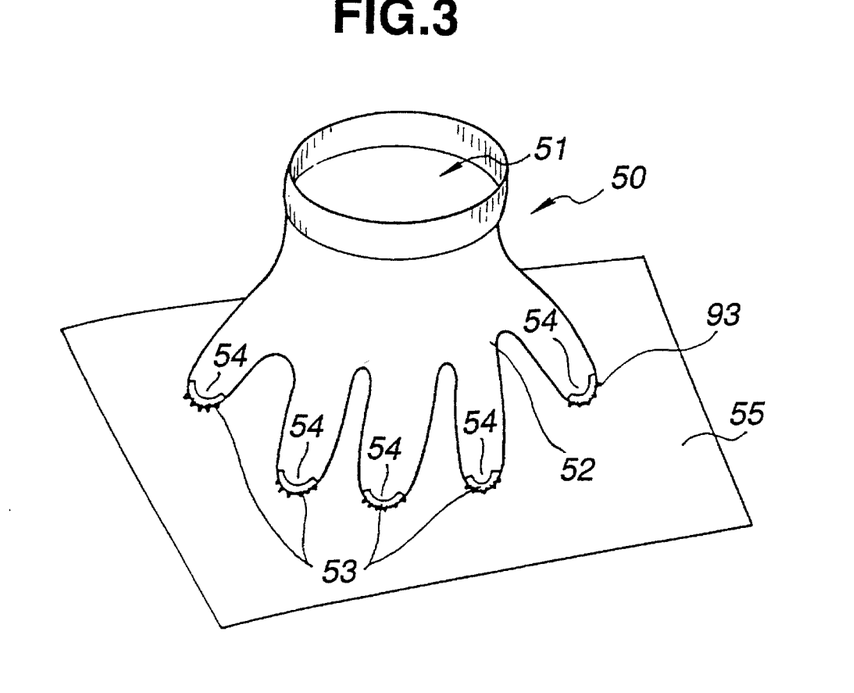
FIG. 3 is a sectional view illustrating the construction of a work glove in accordance with a second embodiment of the present invention.

As shown in FIG. 3, a work glove 50 in accordance with the second embodiment is formed of a hand insertion opening portion 51 formed in such a manner as to maintain a substantially circular shaped opening, and an elastic glove 52 formed in such a manner as to maintain the shape of the hand unless an external force is applied thereto. That is, during normal use of the work glove 50, the elastic glove 52 maintains the shape of a hand and the hand insertion opening portion 51 is open. As shown in the figure, a removable tape, for example, a perchlo tape 53, may be provided on the finger tip portions 54 of the work glove 50, and a sheet-like perchlo tape 55 may be provided on a work table so that the hand insertion opening portion 51 of the work glove 50 stands upright with it's opening upward.

Since a work glove is formed of a hand insertion opening portion and an elastic glove as described above, a hand can be easily inserted into the work glove and easily removed therefrom by relaxing the hand. Two sets of the work gloves may be prepared, and a particular color indicating whether a set of gloves is to be used in a clean or a general area may be applied to each of the two sets of gloves in the same way as in the above-described embodiment so that their workability can be improved. In addition, the work glove may be formed in such a way that it can stand on its own. As such a work glove can be reused after it is cleaned and sterilized, resources can be more efficiently used.

Hitherto, a cover holder has been used only when the covered endoscope 4 is inserted into a cover. However, no consideration is given to the location where a covered endoscope removed from a cover which has been used after an endoscope examination is finished is placed. Therefore, a cover holder is constructed as described below.

Figure 4:
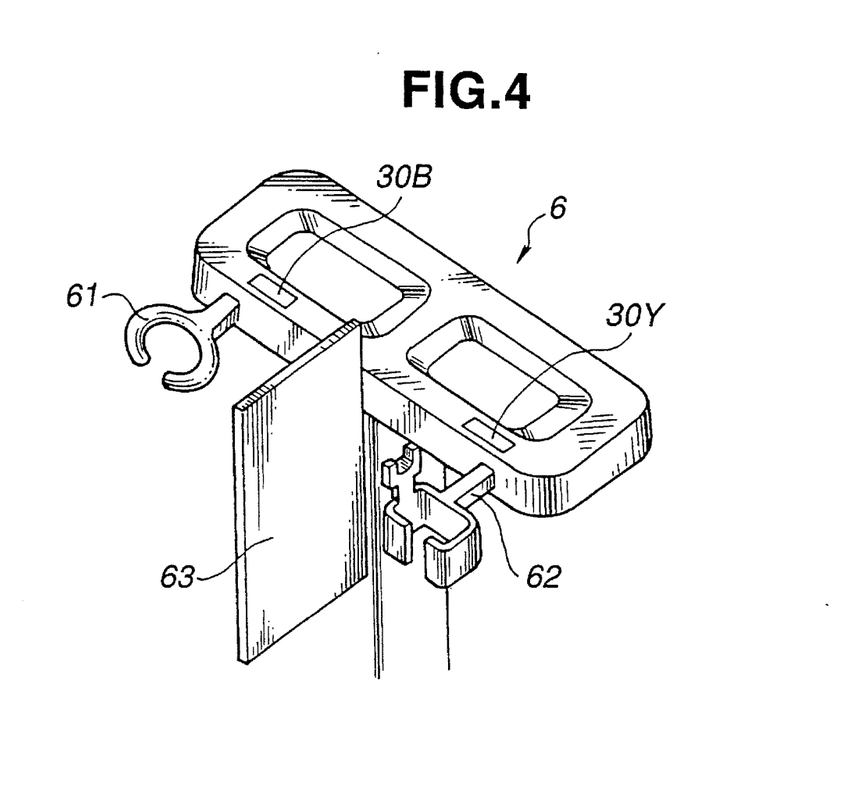
FIG. 4 is a perspective view illustrating the construction of a cover holder in accordance with a third embodiment of the present invention.

As shown in FIG. 4, the cover holder 6 in accordance with the third embodiment is provided with a cover holding portion 61 and a covered endoscope holding portion 62. An division plate 63 is provided between the cover holding portion 61 and the covered endoscope holding portion 62. Further, in the same way as in the above-described first embodiment, the tape 30Y for indicating a general area is affixed on the covered endoscope holding portion side, and the tape 30B for indicating a clean area is affixed on the cover holding portion side.

Since there is no need to prepare a covered endoscope holder for holding the covered endoscope since the cover holder is provided with a cover holding portion and a covered endoscope holding portion as described above, the space of the cover type endoscope apparatus can be saved and workability can be improved.

Covers are stored in a condition in which they are sterilized and put into bags. When the cover type endoscope apparatus is to be used, a person in charge of a clean area takes out a cover. However, because the insertion portion cover portion to which a cover endoscope is inserted is long, there is a risk in that the sterilized state of the insertion portion cover portion cannot be maintained if an inexperienced person handles the insertion portion cover portion. Therefore, the cover endoscope is sometimes mounted in a condition in which the insertion portion cover portion taken out of a bag is inserted beforehand into an overtube which covers the insertion portion cover portion so that the sterilized state of the insertion portion cover portion can be maintained with ease whoever is in charge. However, when the cover endoscope is inserted into an endoscope insertion hole disposed in the insertion portion cover portion inserted into the overtube, the expansion function provided in the insertion portion cover portion cannot be efficiently used. Accordingly, the overtube which covers the insertion portion cover portion is constructed as described below.

Figure 5:
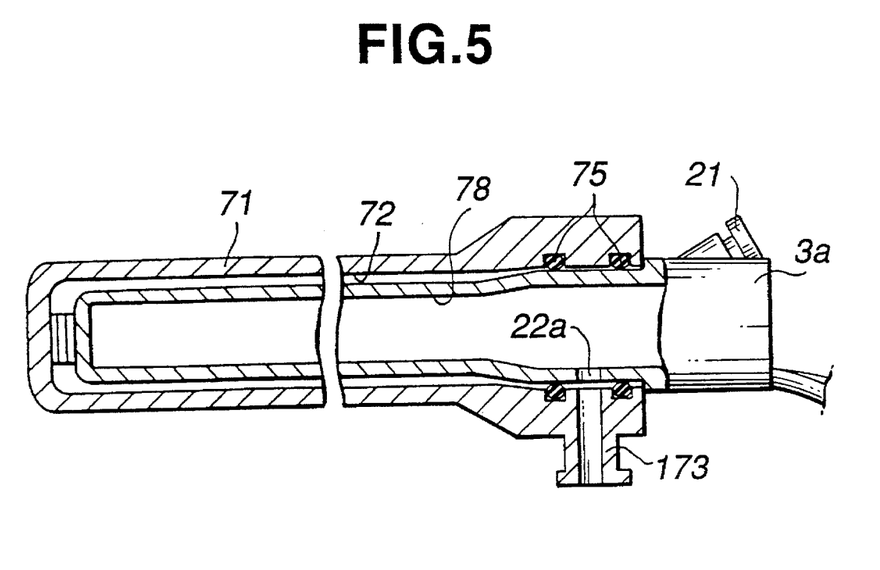
FIG. 5 is s sectional view illustrating an overtube which passes through an insertion portion cover portion of the cover in accordance with a fourth embodiment of the present invention.

As shown in FIG. 5, an overtube 71 in accordance with the fourth embodiment is formed of a cover insertion hole 72 into which the insertion portion cover portion 3a which covers the cover endoscope is inserted and an expansion mouth portion 173 which leads up to the cover insertion hole 72. Two O rings which form an expansion tube for supplying air supplied from the expansion mouth portion 173 formed in the overtube 71 are disposed in the insertion portion cover portion insertion opening side of the cover insertion hole 72.

The overtube 71 formed in the above-described way will now be explained.

Initially, when the insertion portion cover portion 3a is inserted into the cover insertion hole 72, the insertion portion cover portion 3a is brought into close contact between the two O rings 75. Thus, an expansion tube is formed which leads up to an expansion hole 22a formed in the insertion portion cover portion 3a. When air is supplied to the expansion mouth portion 173 formed in the overtube 71, air is supplied to the expansion hole 22a formed in the insertion portion cover portion 3a, causing an endoscope insertion hole 78 of the insertion portion cover portion 3a to expand.

In this way, by providing 0 rings which serve as an air supply tube for the expansion holes of the expansion mouth portion and the insertion portion cover portion in the overtube, even the insertion portion cover portion inserted into the overtube can be expanded easily. As a result, since a sterilized state can be maintained by placing the insertion portion cover portion of the cover endoscope within the overtube immediately before an examination, handling the cover endoscope is easy, the load of the person in charge is reduced, and workability is improved.

Besides, since the insertion portion cover portion is inserted into the overtube and the endoscope insertion hole provided in the insertion portion cover portion is expanded, the insertion portion cover portion can be prevented from being deteriorated due to over-expansion.

Figure 6:
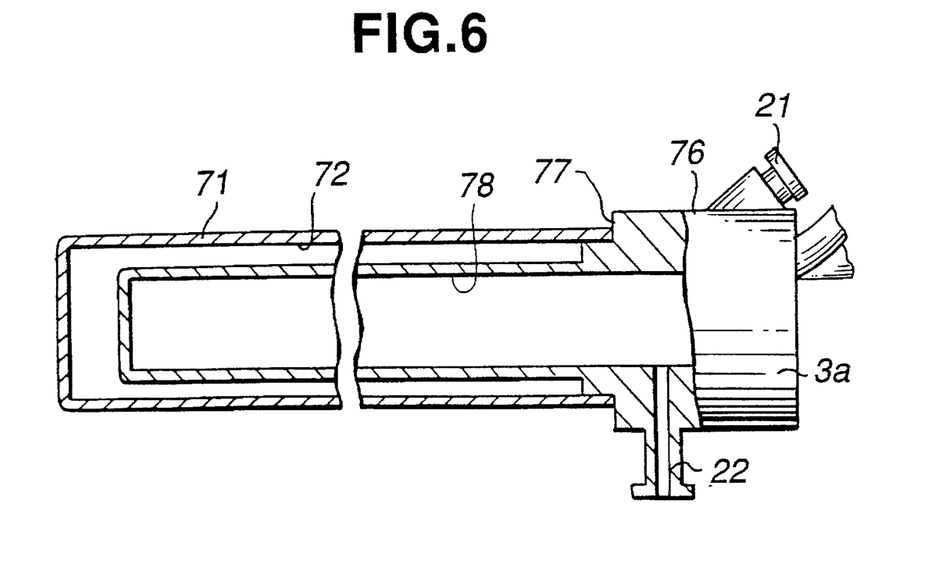
FIG. 6 is a sectional view illustrating a modification of the overtube in accordance with the fourth embodiment of the present invention.

In addition, as shown in FIG. 6, a stepped portion 77 for locking an overtube is formed in a fixation mouth portion 76 of the insertion portion cover portion 3a, and the overtube 71 is locked to the stepped portion 77. As a result, the clean state of the insertion portion cover portion 3a positioned on the tip portion side from the fixation mouth portion 76 of the insertion portion cover portion 3a can be maintained. The endoscope insertion hole 78 of the insertion portion cover portion 3a can be expanded in a condition in which the overtube 71 is mounted.

Covering the operation portion having a complex curved surface or irregular portions of the cover type endoscope with a sheet cover in a liquid-tight manner and in such a manner as to be capable of easily grasping it is a difficult operation requiring great dexterity. For this reason, there has been a demeand for an operation portion cover which is capable of covering the cover endoscope easily in a liquid-tight manner without deteriorating grasping characteristics and maneuverability.

Figure 7:
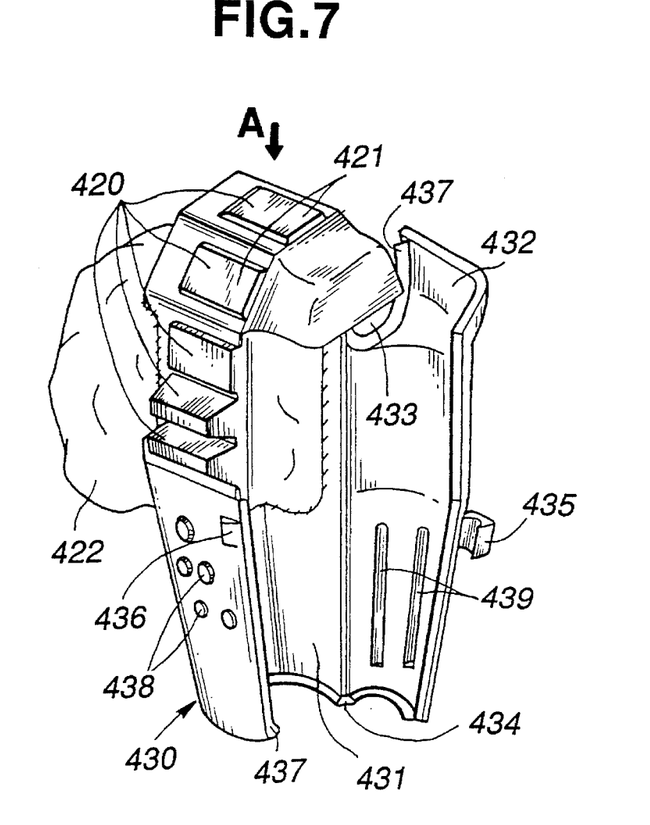
FIG. 7 is a perspective view of an operation portion cover of the cover type endoscope in accordance with a fifth embodiment of the present invention.
Figure 8:
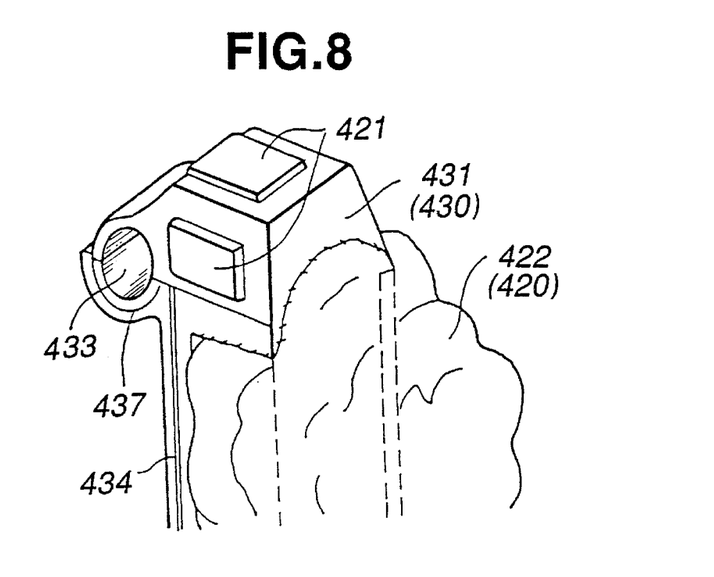
FIG. 8 is a view taken in the direction of the arrow A of FIG. 7.

Accordingly, as shown in FIGS. 7 and 8, an operation portion cover 410 in the fifth embodiment is formed of a soft cover portion 420 for covering a group of control switches 49 and curved operation knobs disposed on an operation portion 41 of the covered endoscope 4, and a hard cover portion 430 for covering the grip portion of the operation portion 41 or the like other than the above. The hard cover portion 430 is shaped in substantially the same shape as the outer shape of the operation portion 41 of the covered endoscope 4. The outer shape is a highly stable shape in which emphasis is placed on gripping characteristics. The hard cover portion 430 is formed of a cover box portion 431 and a cover lid portion 432 so that the operation portion 41 of the covered endoscope 4 can be easily covered with the operation portion cover 410.

A notch 433 is provided in the cover lid portion 432 so that a universal cord extension portion 46a formed in the operation 41 of the covered endoscope 4 is positioned. In the cover box portion 431, a button cover 421 is integrally disposed in a water-tight manner so that it fits the soft cover portion 420 with which the control switches 49 of the operation portion 41 are covered.

A notch is formed on the opposite cover lid portion side of the cover box portion 431 so that a curved operation knob mounted on an operation portion 41 can be arranged. A resin sheet 422 is welded in this notch so that the water-tightness of the endoscope cover 3b can be maintained and the curved operation knob can be manupulated at will.

In addition, the cover box portion 431 is connected to the cover lid portion 432 by means of a hinge portion 434 in the hard cover portion 430, thus the hard cover portion 430 is formed as one piece in which it can be opened and closed as desired. Since a claw portion 435 formed in the cover lid portion 432 is locked to an locking portion 436 formed in the cover box portion 431, the cover lid portion 432 and the cover box portion 431 are made into one piece.

To ensure water-tightness when the cover box portion 431 and the cover lid portion 432 are made into one piece, an elastic sealing member 437 is disposed on the surface on which the cover box portion 431 closely contacts the cover lid portion 432, and the elastic sealing member 437 is disposed on the surface on which the cover lid portion 432 closely contacts the universal cord extension portion.

Figure 9:
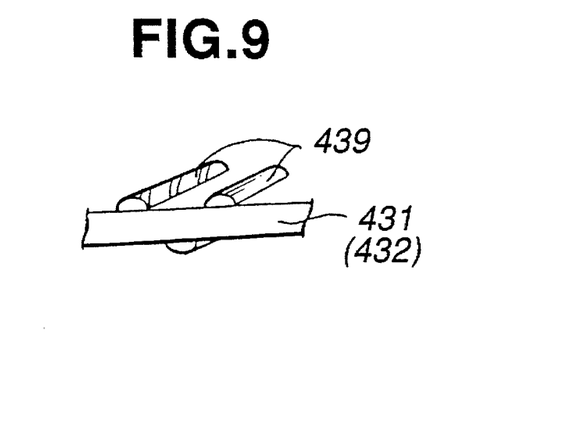
FIG. 9 is a perspective view illustrating a non-slipping member of the operation portion cover of the cover type endoscope.

A plurality of protruding, circular-shaped non-slipping members 438 or bar-shaped non-slipping members 439 shown in FIG. 9 are integrally formed on both the obverse and reverse surfaces of the grip portion of the hard cover portion 430. The non-slipping members 439 formed of an elastic member for preventing positional deviation from the operation portion 41 of the covered endoscope 4 are disposed on both the obverse and reverse surfaces of the cover lid portion 432.

The operation of the operation portion cover 3a constructed as described above will now be explained.

Initially, the cover lid portion 432 of the operation portion cover 3a is fully opened, and the operation portion 41 of the covered endoscope 4 is mounted. At this time, the group of control switches 49 and the curved operation knobs disposed on an operation portion 41 are mounted in accordance with a predetermined position of the soft cover portion 420.

Next, the cover lid portion 432 is closed in accordance with the cover box portion 431. Hereupon, the sealing member 437 and the non-slipping members 439 formed on the inner surface of the cover lid portion 432 are brought into contact with the universal cord extension portion, the operation portion grip portion and the like, increasing the sensation of resistance, making it a little difficult to close the cover lid portion 432 in accordance with the cover box portion 431.

Further, as a result of the cover lid portion 432 being closed, the claw portion 435 formed in the cover lid portion 432 is locked to the locking portion 436 formed in the cover box portion 431, causing the operation portion 41 of the covered endoscope 4 to be covered in a water-tight manner.

Since the operation portion cover is formed of hard and soft cover portions, it can cover the covered endoscope without deteriorating the gripping characteristics and maneuverability of the covered endoscope operation portion. Further, since the hard cover portion is formed of the cover box portion and the cover lid portion, it is possible to considerably shorten the time required to mount a cover in the operation portion of the covered endoscope in a condition in which the water-tightness is maintained, greatly improving the workability. In addition, the sensation of gripping during an operation is stabilized since a non-slipping member for preventing the hand of the operator from slipping is formed in the gripping portion of the operation portion cover and since a non-slipping member for preventing a positional deviation of the covered endoscope operation portion is formed on the inner surface of the cover lid portion.

Next, a modification of the operation portion cover will be explained with reference to FIGS. 10 to 13.

Figure 10:
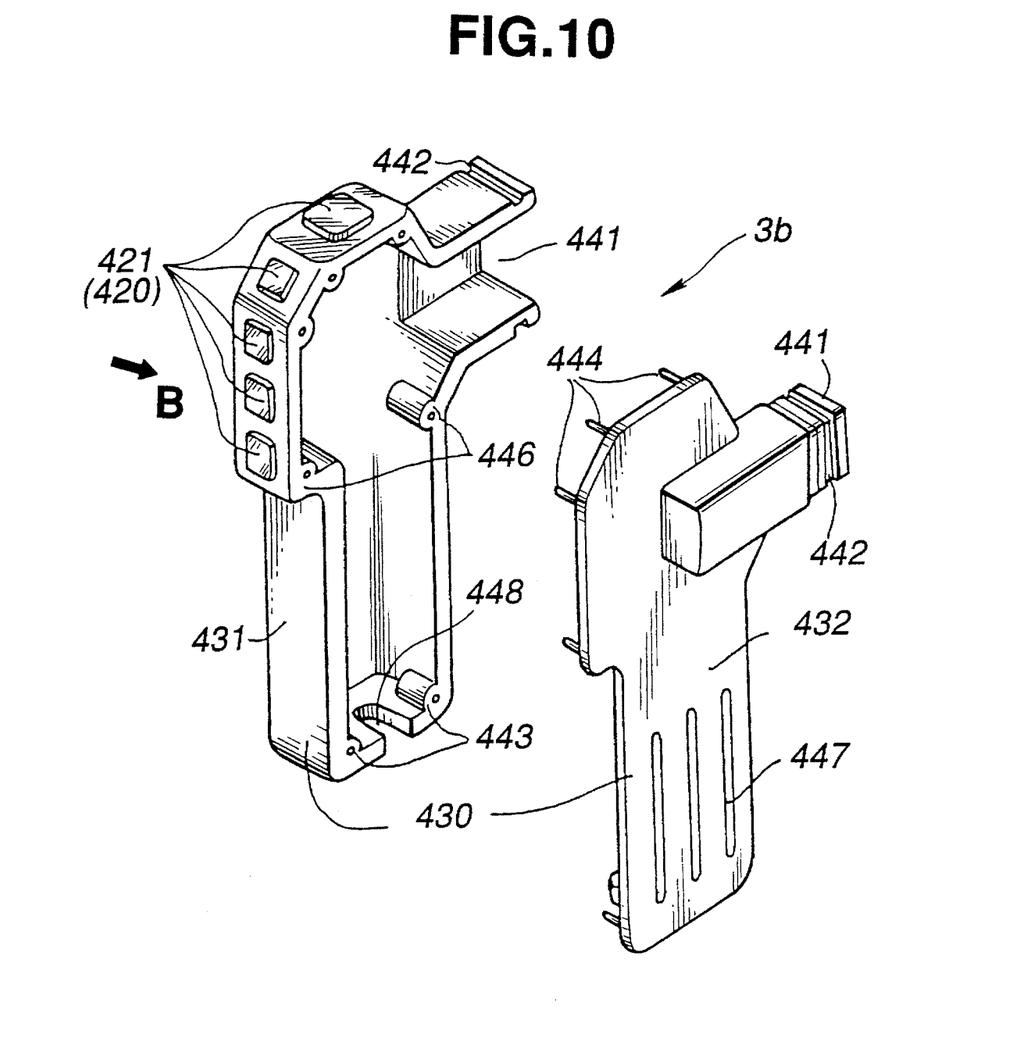
FIG. 10 is a perspective view illustrating the construction of the operation portion cover of the cover type endoscope in accordance with a modification of the fifth embodiment of the present invention.

In this embodiment, the operation portion cover 3a is engineering plastic, such as polypropylene or polyethylene, having excellent resistance to heat and chemicals and having excellent strength.

As shown in FIG. 10, the endoscope cover 3b is separately formed of the cover box portion 431 and the cover lid portion 432. Switch covers 421 formed of mobile silicon rubber and fluorine rubber are disposed in the cover box portion 431 in such a manner as to correspond to the group of control switches 49, thus forming the soft cover portion 420. A universal cord extension portion 441 is formed in the cover box portion 431 and the cover lid portion 432 in the portion corresponding to the universal cord. A locking portion 442 for locking the universal cord cover 3c, or the like is formed around the outer periphery of the extension portion 441.

It is necessary to quickly and integrally form and fix the cover box portion 431 and the cover lid portion 432 of the endoscope cover 3b to the operation portion 41 of the covered endoscope 4. Therefore, a plurality of fixation holes 443 . . . are formed in the cover box portion 431 as means for fixing the cover box portion 431 and the cover lid portion 432 as one piece, and a plurality of projections 444 which are inserted into the fixation holes 443 are formed in the cover lid portion 432.

Figure 11:
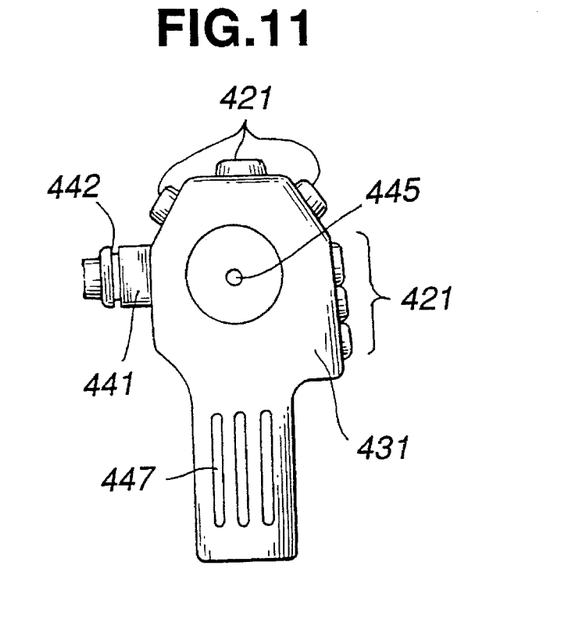
FIG. 11 is a view taken in the direction of the arrow B of FIG. 10.

As shown in FIG. 11, an angle hole 445 from which an angle shaft 48a of the covered endoscope 4 protrudes is formed in the cover box portion 431.

A thin filmy sealing member 446 is provided around the fixation holes 443 disposed in the cover box portion 431. The sealing member 446 is also provided in the angle hole 445 into which the angle shaft 48a is inserted. Thus, they are sealed in such a way that no problem is caused in the rotation of the angle shaft 48a. Also, a plurality of projections 447 which serve as non-slipping members are formed in the gripping portion of the operation portion cover 3b.

Figure 12:
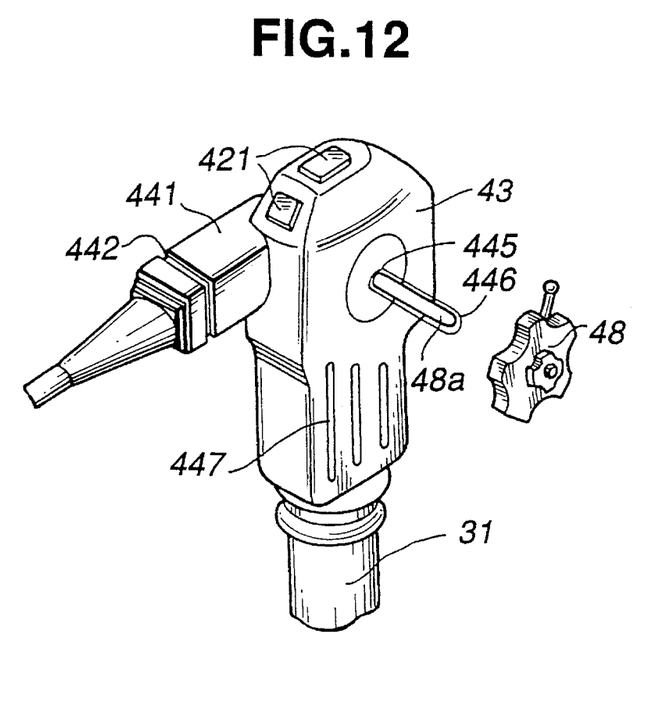
FIG. 12 is a perspective view when an operation portion cover of the cover type endoscope is assembled.
Figure 13:
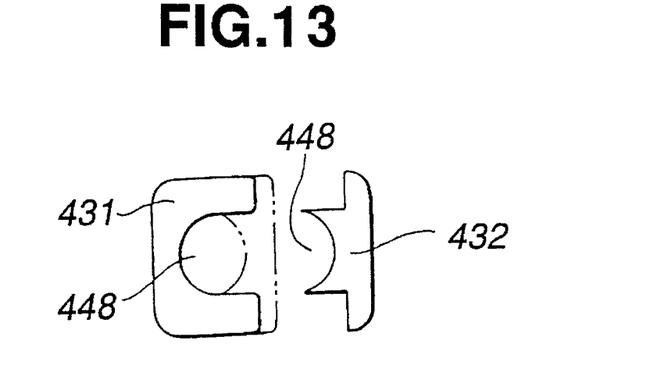
FIG. 13 is an illustration showing a method of connecting the operation portion cover of the cover type endoscope of FIG. 12 to the insertion portion cover cover.

In addition, as shown in FIGS. 12 and 13, in the endoscope cover 3b, an locking portion 448 is disposed in each of the cover box portion 431 and the cover lid portion 432 to make it possible to integrally lock to the fixation mouth portion 76 of the insertion portion cover portion.

Next, the operation of the operation portion cover 3a constructed as described above will be explained.

Initially, the operation portion 41 of the covered endoscope 4 is housed in the cover box portion 431. Next, the projections 444 of the cover lid portion 432 are inserted into the fixation holes 44 of the cover box portion 431. At this time, as shown in FIG. 12, the angle shaft 48a of the covered endoscope 4 protrudes from the angle hole 445 formed in the cover box portion 431 in a condition in which the angle shaft 48a is covered with the sealing member 446. A curved operation knob 48 is fixed to the projecting angle shaft 48a. Finally, the universal cord cover 3c is connected to the locking portion 442 of the universal cord extension portion 441 in a water-tight manner.

As the operation portion cover is divided into a cover box portion and a cover lid portion and formed by engineering plastic having excellent resistance to heat and chemicals and having excellent resistance to repeated bending of hinge by taking into consideration repeated assembly characteristics, water-tightness and workability in the above-described way, it can be repeatedly used as a result of performing a sterilization process, such as ethylene oxide gas sterilization, autoclave sterilization, medical fluid sterilization, or radiation sterilization. This is economical, and resources can be more efficiently used.

Further, since the disposal curved operation knob is not covered with a resin sheet, the sensation of fingers is directly transmitted to the curved operation knob, thus improving maneuverability for a curve.

In addition, as a common operation portion cover is used for a covered endoscope having a plurality of operation buttons of different specifications, it is possible to make common the operation portion of the covered endoscope. The common use of the operation portion cover makes it possible to standardize the operation for covering the covered endoscope and to improve the skill in the operation, and also to eliminate contamination and damage caused by erroneous assembly.

Figure 14:
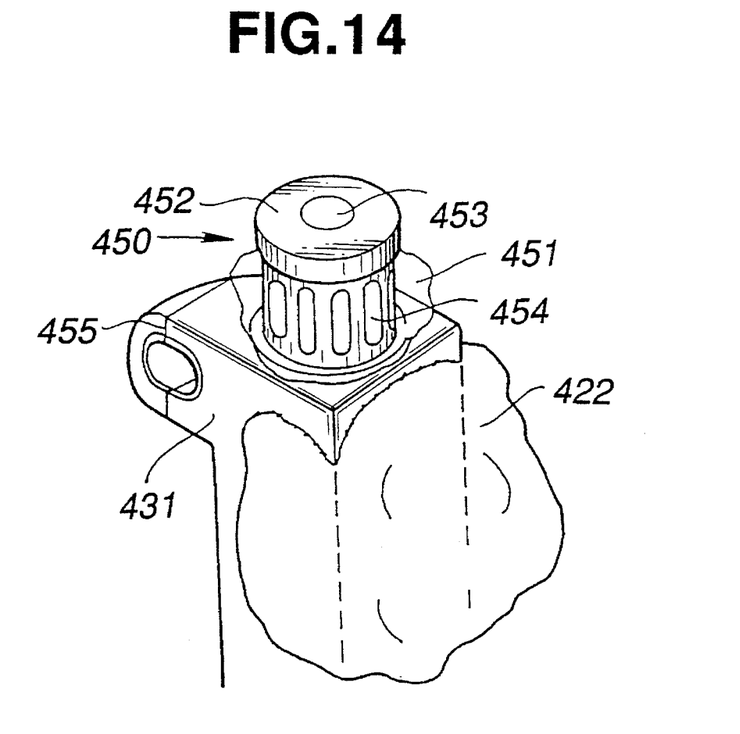
FIG. 14 is a perspective view illustrating the operation portion cover of an optical endoscope in accordance with an application example of the fifth embodiment.

Next, an explanation will be given of an operation portion cover when an optical covered endoscope is used for a covered endoscope as an example of the application of the operation portion cover.

As shown in FIG. 14, the covered endoscope is a fiberscope. In an endoscope cover 3b', an eyepiece 450 of the fiberscope is covered with a soft, thin resin sheet 451, and an eyepiece mounted in the tip portion of the eyepiece 450 is integrally welded with the resin sheet 451.

A transparent plastic eyepiece 453 is disposed in the substantially central portion of an eyepiece cap 452 in a water-tight manner. A diopter adjustment ring 454 of the fiberscope is covered with the resin sheet 451 with an allowance in such a manner as to be rotatable. A notch 455 for permitting the universal cord extension portion to escape is formed lengthwise in the cover box portion 431. Other components are the same as those of the operation portion cover 3b which covers an electronic endoscope, and are given the same reference numerals.

In this way, the operation portion of the optical endoscope can be easily covered in the same manner as the operation portion of the electronic endoscope. Other operations and advantages are the same as those of the operation portion cover which covers the electronic endoscope.

Covering the universal cord extending from the covered endoscope and a plurality of tubes extending from the cover integrally in a water-tight manner is a difficult operation requiring a considerable skill. Therefore, there has been a demand for a universal cord cover which is capable of covering the universal cord extending from the covered endoscope and a plurality of tubes extending from the cover integrally in a water-tight manner.

Figure 15:
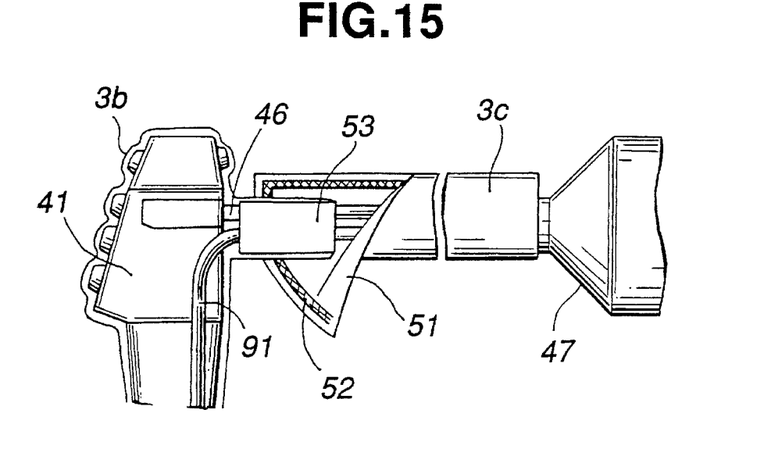
FIG. 15 is an illustration showing means for connecting a universal cord cover in accordance with a sixth embodiment of the present invention.

Therefore, as shown in FIG. 15, the universal cord cover 3c in accordance with the sixth embodiment is the soft, thin resin sheet 51. A bonding portion 52 serving as bonding means 52 is provided on the end surface on one side along the long side of the resin sheet 51 and on the end surfaces on both sides along the short side of the resin sheet 51.

The bonding means 52 has a highly close contact; for example, contact with the obverse and reverse surfaces of the resin sheet 51, or contact with a metallic member or a resin member is excellent.

The operation of the resin sheet 51 formed as described above will now be explained.

The insertion portion 42 and the operation portion 41 of the covered endoscope 4 are covered with the insertion portion cover 3a and the operation portion cover 3b, respectively.

Initially, the universal cord 46 extending from the covered endoscope 4 and the water supply tube 91 extending from the cover 3 are collected together by a tube holder 53 disposed in the vicinity of the operation portion of the covered endoscope 4. Next, the bonding portion 52 provided on an end surface along the short side of the resin sheet 51 is affixed to the tube holder 53, and the bonding portion 52 provided on the other end surface along the short side is affixed to the connector 47 of the universal cord 46. Next, the resin sheet 51 is wound around the tube holder 53 and the connector 47. Hereupon, the bonding portion 52 disposed on both end surfaces of the resin sheet 51 is gradually wound around the tube holder 46 and the connector 47 while the resin sheet 51 is in close contact with them and forms a substantially cylindrical tube. Finally, the bonding portion 52 provided along the long side is bonded thereto, and thus the substantially cylindrical universal cord cover 3a is completed.

As the bonding portion serving as bonding means is provided on the resin sheet which forms the universal cord cover in the above-described way, it is possible to integrally and beautifully bundle a universal cord and a tube quickly and easily so that a covered universal cord cover can be formed.

Figure 16:
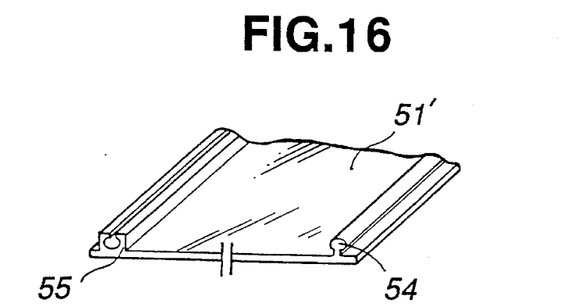
FIG. 16 is a perspective view illustrating the construction of the universal cord cover in accordance with a modification of the sixth embodiment of the present invention.
Figure 17:
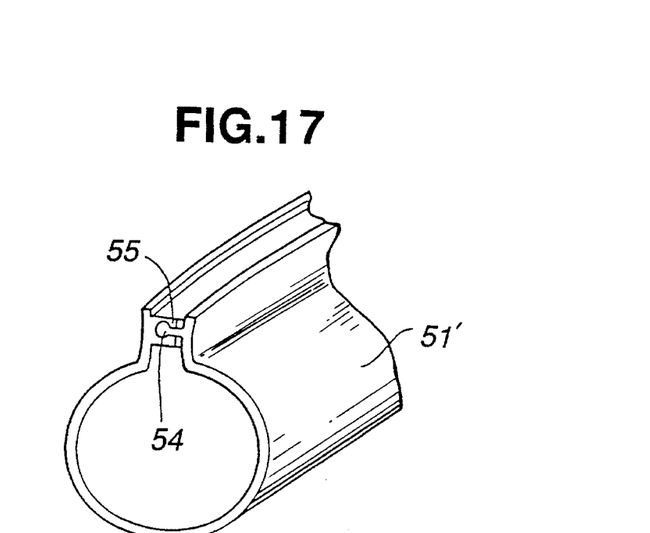
FIG. 17 is a perspective view illustrating a state in which the universal cord cover is mounted in accordance with the modification of the sixth embodiment of the present invention.
Figure 18:
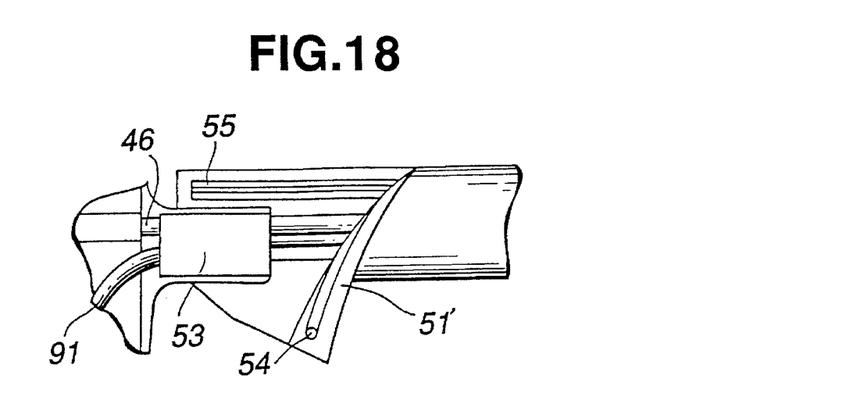
FIG. 18 illustrates a state in which the universal cord cover is mounted in accordance with the modification of the sixth embodiment of the present invention.

Next, another example of the bonding means will be explained with reference to FIGS. 16 to 18.

As shown in the figures, regarding the bonding means 50 disposed in the resin sheet 51, the projection portion 54 formed in the end portion of a resin sheet 51' in place of the bonding portion 52 in accordance with the above-described embodiment fits into a recess 55 to achieve a close contact.

As the bonding means 50 of the resin sheet 51 is formed in such a way that the projection portion 54 is fitted into the recess 55 in the above-described way, the bonding means 50 can be used for a plurality of purposes. Therefore, it is possible to reuse the resin sheet 51 after it is sterilized, and resources can be more efficiently used. Other advantages and operations are the same as in the above-described embodiment.

Figure 19:
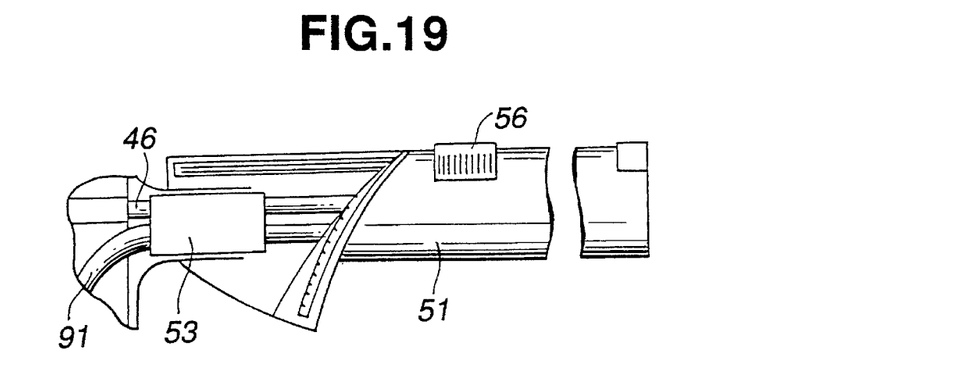
FIG. 19 illustrates a state in which the universal cord cover is mounted in accordance with another modification of the sixth embodiment of the present invention.

It is also possible to obtain the same advantages and operations as those of the resin sheet 51' by providing a fastener 56 as the bonding means 50 in the resin sheet 51, as shown in FIG. 19.

Although the cover provided with a water supply tube have been explained in this embodiment, the tube provided in the cover is not limited to a water supply tube, but a suction tube or an air supply tube may also be provided. An insertion portion cover having no tube may also be used.

In the conventional covered endoscope, when an examination is carried out in combination with X-rays, the tip portion 33 of the cover type endoscope cannot be reflected by X-rays. Therefore, when, for example, lower part digestive organs are examined, it is not easy to confirm where the tip portion of the covered endoscope is positioned in a case where the covered endoscope is moved through the winding organs. Accordingly, the covered endoscope is formed as described below so that a covered endoscope examination can be carried out in combination with X-ray observation.

Figure 20:
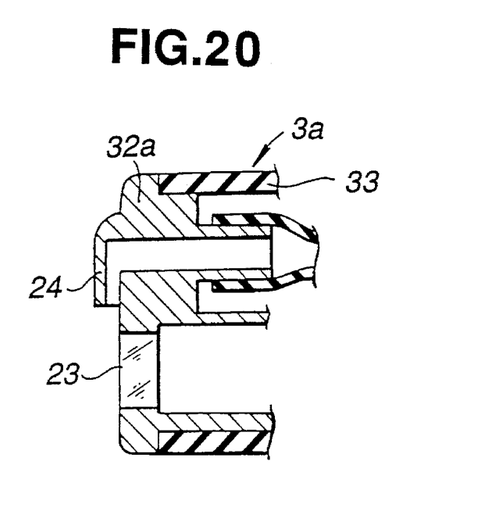
FIG. 20 is a sectional view illustrating the construction of X-ray observation means in the tip portion of the insertion portion cover in accordance with a seventh embodiment of the present invention.
Figure 21:
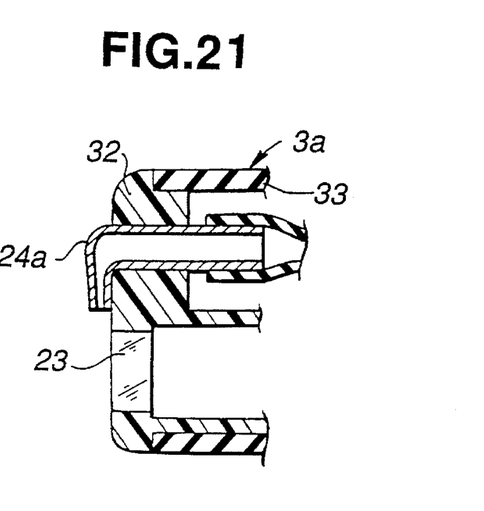
FIG. 21 is a sectional view illustrating another construction of the X-ray observation means in the tip portion of the insertion portion cover in accordance with the seventh embodiment of the present invention.

That is, as shown in FIGS. 20 and 21, in the insertion portion cover 3a in accordance with the seventh embodiment, the tip forming portion 32a is formed from a resin material to which metallic powders are mixed (FIG. 20), or a metallic air and water supply nozzle 24a is disposed in the tip forming portion 32a (FIG. 21).

As the tip forming portion is formed from a resin material to which metallic powders are mixed, the tip portion of the covered endoscope can be reflected as an X-ray image when an endoscope examination is carried out in combination with X-ray observation. As a result, since the operator is able is perform an examination while confirming the tip portion of the covered endoscope, the workability during examination is greatly improved, making it possible to quickly perform an appropriate examination. The tip forming portion and the insertion portion cover integumentum may be made impermeable to X-rays so that the entire cover can be reflected as an X-ray image. A metallic chip may be buried within the tip forming portion instead of mixing metallic powders thereto.

The cover of the covered endoscope may contact mucous membranes or bleeding affected parts during an examination. Therefore, a cover integumentum 33, a tip forming portion 32 of the insertion portion cover 3a, an air and water supply nozzle 24 and the like, shown in FIGS. 20 and 21, are formed from materials compatible with living beings, for example, polysulfone, fluorine resin or silicon resin. The insertion portion cover is formed from silicon rubber, fluorine rubber, thin film Teflon, urethane in part, or the like. Further, metallic powders provided to make the tip forming portion impermeable to X-rays, or metals which form the air and water supply nozzle are formed of metals compatible with living beings. As regions which may contact mucous membranes within body cavities or the like are formed from materials compatible with living beings, a covered endoscope having no infiltration to a patient can be formed.

When an examination is carried out while the insertion portion is bent or twisted in agreement with the shape of body cavities, the covered endoscope installed within the insertion portion cover may deviate axially, deteriorating the optical characteristics considerably.

Figure 22A:
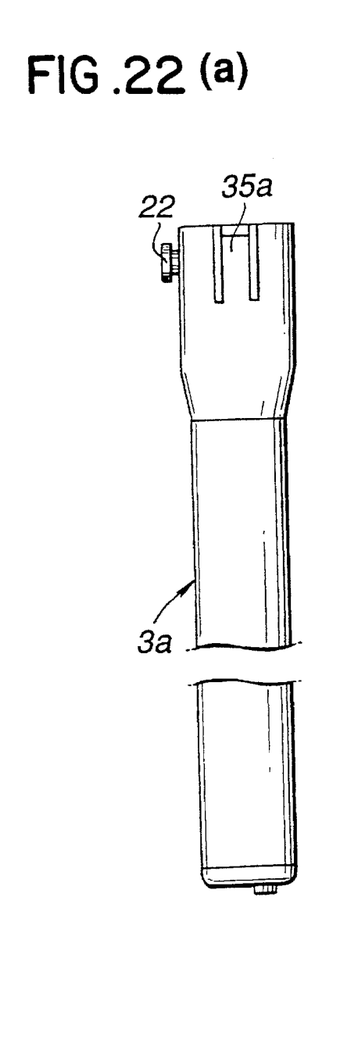
FIG. 22(a) is a front view of the insertion portion cover illustrating mounting/dismounting means in accordance with an eighth embodiment of the present invention.
Figure 22B:
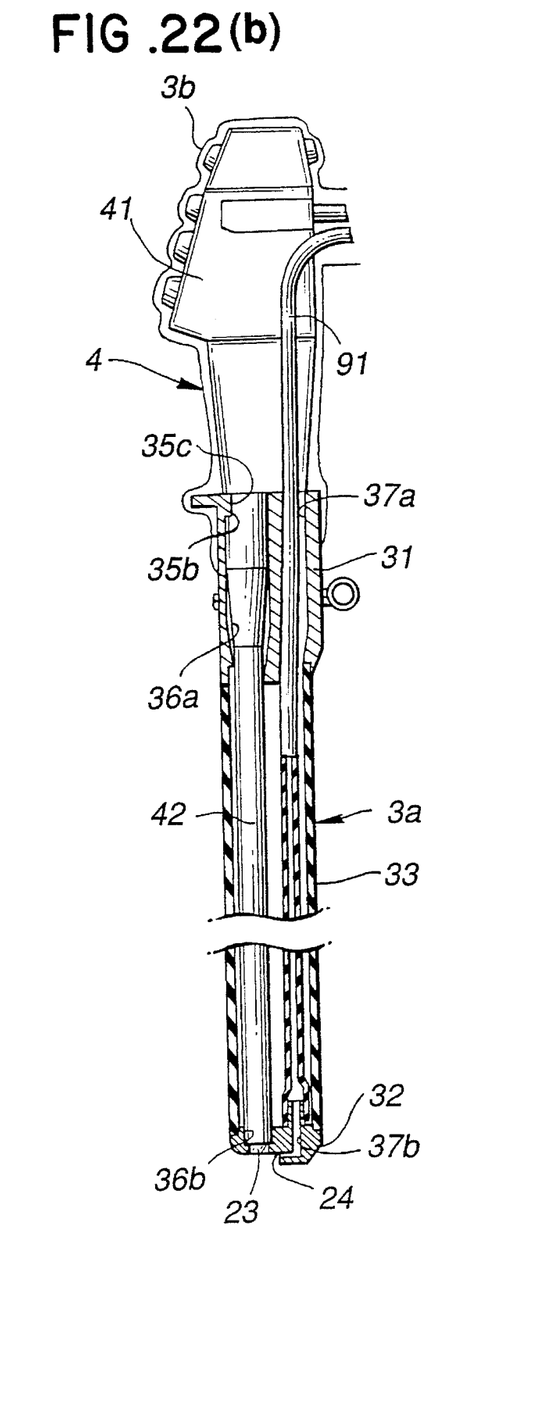
FIG. 22(b) is a sectional view illustrating the construction of the mounting/dismounting means in accordance with the eighth embodiment of the present invention.

Therefore, as shown in FIG. 22, a removable portion 35 having a clicking mechanism is disposed on the side of a fixation mouth portion 31 of the insertion portion cover 3a in accordance with an eighth embodiment so that the fixation mouth portion 31 and the operation portion 41 (or a hard operation portion cover) of the covered endoscope 4 can be reliably mounted. An expansion tube 22 protrudes from the side of the fixation mouth portion 31.

In the removable portion 35, an elastic portion 35a is formed in the fixation mouth portion 31, and a projection 35b is formed in the elastic portion 35a. Also, a recess 35c is formed at a position corresponding to the projection 35b in the vicinity of the operation portion of the covered endoscope 4.

An endoscope insertion hole 36a into which the insertion portion 42 of the covered endoscope 4 is inserted, and a water supply hole 37a are formed in the fixation mouth portion 31. An endoscope positioning hole 36b into which the tip portion 42 of the covered endoscope 4 is inserted and a water supply hole 37b corresponding to the water supply hole 37a are formed in the tip forming portion 32 facing the fixation mouth portion 31. An observation window 23 and the air and water supply nozzle 24 are disposed in the tip portion of the tip forming portion 32.

Next, the operation of the cover type endoscope 2 in which the removable means 35 is formed as described above will be explained.

When the covered endoscope 4 is inserted into the insertion portion cover 3a and reaches a predetermined position, the projection 35b of the elastic portion 35a provided in the fixation mouth portion 31 is fixed, with a click, to the recess 35c formed in the covered endoscope 4 as one piece.

When the covered endoscope 4 is removed from the insertion portion cover 3a, the elastic portion 35a provided in the fixation mouth portion 31 is lifted by fingers, causing the projection 31b to be removed from the corresponding recess 35c so as to remove the covered endoscope 4 from the insertion portion cover 3a.

As the removable means 35 is formed in the cover type endoscope 2 in the above-described way, it is possible to make sure that the covered endoscope 4 has been reliably mounted in the insertion portion cover 3a. In addition, since there is no risk in that the covered endoscope and the insertion portion cover do not deviate axially, endoscope images can always be obtained stably.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included with the spirit and scope of the claims. The following claims are to be accorded the broadest interpretation, so as to encompass all such modifications and equivalent structures and functions.

What is claimed is:

1. A cover type endoscope apparatus, comprising:

a cover; and a covered endoscope which is inserted into this cover and used, wherein an operation portion cover for covering the operation portion of said covered endoscope is formed of a hard cover portion for covering the gripping portion of the operation portion of said covered endoscope and a soft cover portion for covering control switches disposed in the operation portion of said covered endoscope.

2. A cover type endoscope apparatus according to claim 1, wherein the inner surface of said hard cover portion is shaped substantially the same as the outer surface of said covered endoscope, and said covered endoscope has an outer shape which is easy to grip and has non-slipping means.

3. A cover type endoscope apparatus according to claim 1, wherein non-slipping means is disposed on the operation portion cover.

4. A cover type endoscope apparatus according to claim 3, wherein said non-slipping means are projected and recessed portions which are integrally formed on both the obverse and reverse surfaces of the hard cover portion.

5. A cover type endoscope apparatus according to claim 3, wherein said non-slipping means is an elastic member disposed on both the obverse and reverse surfaces of the hard cover portion.

6. A cover type endoscope apparatus according to claim 3, wherein said non-slipping means is disposed on an inside surface touching the operation portion cover.

7. A cover type endoscope apparatus according to claim 3, wherein said non-slipping means is disposed on an outside surface at which a hand of an operator touches.

8. A cover type endoscope apparatus according to claim 1, wherein said hard cover portion is formed of a cover box portion and a cover lid portion, the cover box portion being connected to the cover lid portion by means of a locking member so that the hard cover portion can be opened and closed as desired.

9. A cover type endoscope apparatus according to one of claims 8, or 10, wherein a sealing member is disposed in the opening/closing portion formed of said box portion and said lid portion.

10. A cover type endoscope apparatus according to claim 1, wherein said hard cover portion is separately formed of a box portion and a lid portion so that it can be assembled and disassembled as desired.

11. A cover type endoscope apparatus according to claim 1, wherein said soft cover portion is welded with the hard cover portion in a water-tight manner.

12. A cover type endoscope apparatus according to claim 1, wherein the soft cover portion is a transparent cover.

13. A cover type endoscope apparatus according to claim 1, wherein the cover for covering a group of buttons in said soft cover portion is formed of elastic members.

14. A cover type endoscope apparatus according to claim 1, wherein said hard cover portion has resistance to sterilization ethylene oxide, to radiation, to chemicals and to autoclave.

15. A cover type endoscope apparatus according to claim 1, wherein said operation portion cover includes a soft cover portion for housing a bending operation portion provided in said covered endoscope.

16. A cover type endoscope apparatus according to claim 1, wherein said soft cover portion covers a bending operation portion of said covered endoscope.

17. A cover type endoscope apparatus according to claim 1, wherein said soft cover portion covers tube control switches of said covered endoscope.

18. A cover type endoscope apparatus according to claim 1, wherein said soft cover portion covers image control switches of said covered endoscope.

* * * * *